US 11,766,429 B1

United States Patent
Sanberg et al.

(10) Patent No.: US 11,766,429 B1
(45) Date of Patent: Sep. 26, 2023

(54) NICOTINIC RECEPTOR ANTAGONISTS AND PIOGLITAZONE AS THERAPEUTIC AGENTS FOR COVID-19

(71) Applicant: University of South Florida, Tampa, FL (US)

(72) Inventors: Paul Ronald Sanberg, Spring Hill, FL (US); Christian Bernard Brechot, Tampa, FL (US); Shyam S. Mohapatra, Lutz, FL (US); Subhra Mohapatra, Lutz, FL (US)

(73) Assignee: University of South Florida, Tampa, FL (US)

( * ) Notice: Subject to any disclaimer, the term of this patent is extended or adjusted under 35 U.S.C. 154(b) by 107 days.

(21) Appl. No.: 17/446,021

(22) Filed: Aug. 26, 2021

Related U.S. Application Data

(60) Provisional application No. 63/070,500, filed on Aug. 26, 2020.

(51) Int. Cl.
| | | |
|---|---|---|
| *A61K 31/4439* | (2006.01) | |
| *A61P 31/14* | (2006.01) | |
| *A61K 31/13* | (2006.01) | |

(52) U.S. Cl.
CPC .......... *A61K 31/4439* (2013.01); *A61K 31/13* (2013.01); *A61P 31/14* (2018.01)

(58) Field of Classification Search
CPC ..... A61K 31/4439; A61K 31/14; A61K 31/13
See application file for complete search history.

(56) References Cited

U.S. PATENT DOCUMENTS

| | | | | |
|---|---|---|---|---|
| 5,686,448 A | * | 11/1997 | Baldone ............. | A61K 31/4025 514/642 |
| 2020/0179367 A1 | * | 6/2020 | Williams ................. | A61P 7/00 |

FOREIGN PATENT DOCUMENTS

| | | |
|---|---|---|
| WO | 99/07378 A1 | 2/1999 |

OTHER PUBLICATIONS

Changeux, J-P et al. A nicotinic hypothesis for Covid-19 et ses implications preventives et therapeutiques. Comptes Rendus Biologies (2020) vol. 343, Issue 1, pp. 1768-3238.
Shytle, R.D. et al. Mecamylamine (Inversine): an old antihypertensive with new research directions. Journal of Human Hypertension (2002) 16, 453-457.
Sencanski, M. et al. Drug Repurposing for Candidate SARS-Co V-2 Main Protease Inhibitors by a Novel In Silico Method. Molecules (2020) 25, 3830.
Korner, R.W. et al. Of Mice and Men: The Coronavirus MHV and Mouse Models as a Translational Approach to Understand SARS-Co V-2. Viruses 2020, 12, 880.
Papke, R.L. et al. Analysis of Mecamylamine Stereoisomers on Human Nicotinic Receptor Subtypes. The Journal of Pharmacology and Experimental Therapeutics, 2001, vol. 297, No. 2, pp. 646-656.
Carboni, E. et al. Can pioglitazone be potentially useful therapeutically in treating patients with COVID-19? Medical Hypotheses 140 (2020) 109776.
Sanberg, P.R. et al. Treatment of Tourette's syndrome with mecamylamine. Lancet, Aug. 1998. vol. 352, Issue 9129, pp. 705-706.
Young, J.M. et al. Mecamylamine: New Therapeutic Use and Toxicity/Risk Profile. Clinical Therapeutics (2001), vol. 23, No. 4, pp. 532-565.
Huang C. et al. Clinical features of patients infected with 2019 novel coronavirus in Wuhan, China. Lancet 2020; 395 (10223): 497-506.
Mehta P. et al. COVID-19: consider cytokine storm syndromes and immunosuppression. The Lancet 2020; 395 (10229): 1033-4.
Xie, X. et al. Role of adipocyte mitochondria in inflammation, lipemia, and insulin sensitivity in humans: effects of pioglitazone treatment. International Journal of Obesity (Lond) Aug. 14, 2017.
Qiu D. and Xiang-Nan Li XN. Pioglitazone inhibits the secretion of proinflammatory cytokines and chemokines in astrocytes stimulated with lipopolysaccharide. Int J Clin Pharmacol Ther Sep. 2015;53(9):746-52.
Kutsukak, M. et al. Pioglitazone attenuates lung injury by modulating adipose inflammation. J Surg Res. Jun. 15, 2014;189(2):295-303.
Aoki, Y. et al. Pioglitazone, a peroxisome proliferator-activated receptor gamma ligand, suppresses bleomycin-induced acute lung injury and fibrosis. Respiration. 2009;77(3):311-9.
Barbarin, V. et al. The role of pro- and anti-inflammatory responses in silica-induced lung fibrosis. Respiratory Research. Feb. 2005;6(1):112.
Rubin, R. As Their Numbers Grow, COVID-19 "Long Haulers" Stump Experts, JAMA, Oct. 13, 2020, vol. 324, No. 14:1381-1383.
Martin, B.R. et al. What is the nature of mecamylamine's antagonism of the central effects of nicotine? Biochemical Pharmacology, vol. 38, Issue 20, Oct. 15, 1989, pp. 3391-3397.
Newhouse, P.A. et al. Age-Related Effects of the Nicotinic Antagonist Mecamylamine on Cognition and Behavior. Neuropsychopharmacology 1994, vol. 10, No. 2, pp. 93-107.
Pickworth, W.B. et al. Mecamylamine reduces some EEG effects of nicotine chewing gum in humans. Pharmacology Biochemistry and Behavior, vol. 30, Issue 1, May 1988, pp. 149-153.
Gitelman, D.R. et al. Muscarinic and nicotinic contributions to cognitive function and cortical blood flow. Neurobiology of Aging, vol. 13, Issue 2, Mar.-Apr. 1992, pp. 313-318.

* cited by examiner

*Primary Examiner* — Timothy R Rozof
(74) *Attorney, Agent, or Firm* — Michele L. Lawson; Smith & Hopen, P.A.

(57) ABSTRACT

A method of treating severe acute respiratory syndrome coronavirus 2 (SARS-CoV-2), otherwise known as COVID-19, infection by administering nicotinic receptor antagonists and/or PPAR-γ agonists is presented. A combination of mecamylamine, or an isomer thereof, and pioglitazone synergistically reduces replication of SARS-CoV-2 in virus-infected cells and also synergistically reduces inflammatory cytokines such as IL-6, IL-β, and TNFα, which have been associated with SARS-CoV-2 infection.

12 Claims, 10 Drawing Sheets

| Molecules | Binding Score | Involved Residues | Remark |
|---|---|---|---|
| Pioglitazone | -6.8 | • Arg403: major binding residue to induce cell entry<br>• Lys353:e located on ACE2 that facilitates entry with RBD. | Pioglitazone has high potential to prevent RBD and ACE2 interaction. |
| Mecamylamine | -5.8 | • Asp467: this residue does not interact with ACE2 to facilitate entry. Based on it position it seems to play a role with other interacting receptors just as Furin or TMPSSR.<br>• Arg454: This residue is a trademark target for chloroquine which is an early reported inhibitor for SARS-COV2. | mecamylamine would be a great support inhibitor for pioglitazone given its explicitly distinct target. There could be a synergistic effect |

Fig. 4A-D

Experimental Groups
1. Mock 4
2. Control 4
3. PG 4
4. Mec 4
5. PG+Mec 4
6. Mec Iso 4
7. PG+ Mec Iso 4

Dose
PG- 2mg/kg
Mec/Iso – 2 mg/kg

Parameters Measured
Temperature
Body weight

Organs
Brain, lungs, eyes, spleen
serum-blood

Fig. 8A-F

| combination index | | | | | | | |
|---|---|---|---|---|---|---|---|
| | Brain | | | | | | |
| | PG | Mec | PG+Mec | | PG | Mec iso | PG+Mec iso |
| MHV N | 0.655614 | 0.305154 | 0.755323 | | 0.655614 | 0.352062 | 0.829712 |
| IL-6 | 0.699233 | 0.310728 | 0.898095 | | 0.699233 | 0.352655 | 0.843331 |
| TNFa | 0.592084 | 0.325704 | 0.616512 | | 0.592084 | 0.232111 | 0.733336 |
| IFNg | 0.620956 | 0.418805 | 0.921426 | | 0.620956 | 0.466402 | 0.886848 |
| | Lungs | | | | | | |
| | PG | Mec | PG+Mec | | PG | Mec iso | PG+Mec iso |
| MHV N | 0.483414 | 0.224349 | 0.630254 | | 0.483414 | 0.31465 | 0.467879 |
| IL-6 | 0.422028 | 0.155872 | 0.621611 | | 0.422028 | 0.298924 | 0.558412 |
| TNFa | 0.343719 | 0.235117 | 0.607453 | | 0.343719 | 0.192945 | 0.478771 |
| IFNg | 0.627305 | 0.379924 | 0.522673 | | 0.627305 | 0.492962 | 0.705951 |

Fig. 9

NICOTINIC RECEPTOR ANTAGONISTS AND PIOGLITAZONE AS THERAPEUTIC AGENTS FOR COVID-19

CROSS REFERENCE TO RELATED APPLICATIONS

This application is a nonprovisional of and claims priority to U.S. Provisional Patent Application Ser. No. 63/070,500, entitled "Nicotinic Receptor Antagonists as a Therapeutic Agent for Covid-19", filed Aug. 26, 2020, the contents of which are hereby incorporated by reference into this disclosure.

FIELD OF INVENTION

This invention relates to treatment and/or prevention of coronaviruses. Specifically, the invention provides a method of preventing and/or treating severe acute respiratory syndrome coronavirus 2 (SARS-CoV-2) using nicotinic receptor antagonists such as mecamylamine (or isomers thereof) and/or PPAR-γ agonists such as pioglitazone.

BACKGROUND OF THE INVENTION

Given the magnitude of the global pandemic for severe acute respiratory syndrome coronavirus 2 (SARS-CoV-2), otherwise known as COVID-19, there is extreme urgency to find effective treatments and preventatives. Currently, there is no specific efficacious treatment for COVID-19. In general, treatment consists of supportive care such as fluid replacement therapy or respiratory support in critically ill patients. In some instances, antiviral therapy with a drug such as remdesivir has been used to increase recovery time. Monoclonal antibody therapy has presented some success, however the therapy must be administered within 7 days of the onset of symptoms and is most effective on mild to moderate cases of COVID-19.

Nicotinic Acetylcholine Receptors (nAChR)

Changeux et al. (2020), incorporated herein by reference, hypothesized that nicotinic acetylcholine receptors (nAChR) play a role in the pathophysiology of severe acute respiratory syndrome coronavirus 2 (SARS-CoV-2), otherwise known as COVID-19. Changeux et al. show evidence that beta-coronaviruses, such as SARS-CoV-1 and MERS-CoV, invade the central nervous system (CNS). There is a high similarity between SARS-CoV-1 and SARS-CoV-2 (COVID-19). Other researchers have found that angiotensin converting enzyme 2 (ACE2) is a principal receptor molecule for COVID-19. In the brain ACE2 is expressed in both the neurons and glia and there is a possible contribution of acetylcholine receptors in ACE2 regulation. Changeux et al. propose that the COVID-19 virus could enter the body through neurons of the olfactory system and/or through the lung. The difference in entry point could lead to the difference in clinical symptoms observed in different patients. Previous researchers have shown that a broad diversity of viruses can enter the olfactory epithelium and eventually progress in a retrograde manner to the reticular neurons projecting to the olfactory bulbs. (Changeux 2020)

The nAChR pathway may also be implicated in COVID-19 inflammatory syndrome.

While certain selective cytokine blockers have been proposed, a nicotinic receptor antagonist may act earlier than anti-cytokine therapies by modulating the ACE2-nAChR interaction. nAChRs are also present in the lung epithelium which may act as possible targets for COVID-19 infection of the lung, concomitantly with and/or as a consequence of the neuro-infection. (Changeux 2020)

Further, there is some structural evidence that the SARS-CoV-2 virus is a nicotinic receptor antagonist in that the cryo-EM structure of the trimeric SARS-CoV-2 spike has an exposed loop homologous to the rabies virus (RABV) neurotoxin-like region which has been found to inhibit acetylcholine responses of $\alpha 4\beta 2$ nAChRs in vitro. (Changeux 2020)

As noted above, COVID-19 may be an nAChR disease that can be prevented and/or treated by nAChR antagonists. Changeux et al. also indicate that nicotine may be a potential preventative agent against COVID-19 infection by competing with the virus for binding to the nAChRs. (Changeux 2020)

Mecamylamine

Mecamylamine is a well-known anti-hypertensive that blocks sympathetic ganglia transmission which has shown efficacy for blocking nAChRs in the brain. Mecamylamine blocks nAChRs via interactions with constituent alpha and beta subunits of the nAChR. At higher doses (30-90 mg/day), mecamylamine causes unfavorable side effects. However, at smaller doses, the drug has been found effective for various therapies without the unfavorable side effects and has been used as an aid to stop smoking as noted in Shytle et al. (2002), herein incorporated by reference.

The inventors have previously studied the use of nicotinic receptor antagonists, such as mecamylamine, as therapies for various neuropsychiatric disorders including, but not limited to, Tourette's syndrome, schizophrenia, depression, bipolar disorder, tremors, attention deficit hyperactivity disorder (ADHD), obsessive-compulsive disorder (OCD), hemidystonia, rage outbursts and tardive dyskinesia as noted in PCT International Publication No. WO 99/07378, Sanberg et al. 1998, and Young et al. 2001, herein incorporated by reference. Low doses of mecamylamine have been effective in in the CNS while chronic administration at very high doses is limited by acute toxicity. (Young 2001)

Papke et al. 2001, incorporated herein by reference, previously found that while both stereoisomers of mecamylamine are effective with regard to inhibition, the S-(+)-mecamylamine isomer may be preferable for a therapeutic application. Papke et al. compared R-(−)-mecamylamine and S-(+)-mecamylamine on human $\alpha 3\beta 4$, $\alpha 4\beta 2$, $\alpha 3\beta 2$ and $\alpha 7$ receptors. They found both isomers as well as the racemic mixture of mecamylamine were selective for neuronal nAChRs over muscle-type nAChRs and that the stereoisomers are noncompetitive inhibitors of neuronal nAChRs.

Pioglitazone

There is growing evidence that some patients having severe COVID-19 exhibit a hyper-inflammatory condition known as a cytokine storm. Studies have found that SARS-CoV-2 infection increased plasma IL-1B, IL-1RA, IL-7, IL-8, IL-9, IL-10, basic FGF, GMCSF, IFNγ, IP10, MCP1, MIP1A, MIP1B, PDGF, TNFα, and VEGF concentrations. However, ICU (intensive care unit) patients at severe stage of disease exhibited higher plasma levels of IL-2, IL-7, IL-10, GCSF, IP10, MCP-1, MIP1A and TNFα as compared to non-ICU patients. (Huang C, Wang Y, Li X, et al. Clinical features of patients infected with 2019 novel coronavirus in Wuhan, China. Lancet 2020; 395(10223):497-506; Mehta P, McAuley D F, Brown M, Sanchez E, Tattersall R S, Manson J J. COVID-19: consider cytokine storm syndromes and immunosuppression. The Lancet 2020; 395(10229):1033-4).

Pioglitazone is an FDA approved drug used for treating insulin resistance in diabetic patients. The drug belongs to the family of thiazolidinediones (TZDs) and is known for producing an anti-inflammatory effect shortly after starting therapy. Specifically, pioglitazone (30-45 mg/day) has been shown to significantly reduce IL-6 and TNFα levels in insulin resistant patients. (Xie X, Sinha S, Yi Z, et al. Role of adipocyte mitochondria in inflammation, lipemia, and insulin sensitivity in humans: effects of pioglitazone treatment. Int J Obes (Lond) 2017 Aug. 14). Pioglitazone was also found to inhibit secretion of pro-inflammatory cytokines and increase secretion of anti-inflammatory cytokines. (Qiu D, Li X N. Pioglitazone inhibits the secretion of proinflammatory cytokines and chemokines in astrocytes stimulated with lipopolysaccharide. Int J Clin Pharmacol Ther 2015 September; 53(9):746-52).

Pioglitazone has also been reported to significantly reduce IL-6 and TNFα mRNA expression to attenuate lung injury. (Kutsukake M, Matsutani T, Tamura K, et al. Pioglitazone attenuates lung injury by modulating adipose inflammation. J Surg Res. 2014; 189(2):295-303). Other studies propose that pioglitazone may exert a direct effect on lung inflammation and fibrosis. (Aoki Y, Maeno T, Aoyagi K, et al. Pioglitazone, a peroxisome proliferator-activated receptor gamma ligand, suppresses bleomycin-induced acute lung injury and fibrosis. Respiration. 2009; 77(3):311-9; Barbarin V, Nihoul A, Misson P, et al. The role of pro- and anti-inflammatory responses in silica-induced lung fibrosis. Respir Res. 2005; 6:112).

Carboni et al. proposed using pioglitazone as a potential treatment for COVID-19 infection. They noted that studies have shown that in patients hospitalized with COVID-19, a majority have exhibited several inflammation parameters, such as increased IL-6 levels. Further comorbidities such as diabetes, hypertension, and cardiovascular disorders are risk factors for COVID-19. Such comorbidities are indicative of general inflammation associated with metabolic syndrome and lipid profile alteration. Pioglitazone has been shown to improve such inflammatory conditions and reduce markers of inflammation such as IL-6. (Carboni, E. et al., Can pioglitazone be potentially useful therapeutically in treating patients with COVID-19?, Medical Hypotheses, 140 (2020) 109776). Currently, there are at least 2 clinical trials using pioglitazone to treat COVID-19 in patients also having diabetes.

Given the lack of available treatments for COVID-19, what is needed is a composition that is efficacious as a treatment and/or preventative for infection by SARS-CoV-2 virus.

SUMMARY OF INVENTION

The inventors found a nicotinic receptor antagonist, such as mecamylamine or mecamylamine isomer, is useful to block binding of the SARS-CoV-2 virus to nAChR receptors and thus act as a therapeutic agent for COVID-19. The binding of the nicotinic receptor antagonist aids in the CNS response to COVID-19 symptoms such as headache, vomiting, anosmia, ageusia, and nausea.

The inventors discovered a combination of mecamylamine or mecamylamine isomer with pioglitazone exhibited a synergistic effect in reducing MHV4 replication in vivo. This synergistic effect can be translated to a similar synergistic effect for the combination of drugs being used against SARS-CoV-2 in humans.

In an embodiment, a method of treating severe acute respiratory syndrome coronavirus 2 (SARS-CoV-2) in a patient in need thereof is presented comprising: administering to the patient in need thereof a therapeutically effective amount of a composition comprising a nicotinic receptor antagonist; a peroxisome proliferator activated receptor gamma (PPAR-γ) agonist; and a pharmaceutically acceptable carrier. The nicotinic receptor antagonist and the PPAR-γ agonist act synergistically to reduce SARS-CoV-2 replication in virus-infected cells of the patient. The composition may reduce at least one neurological, cardiovascular, or inflammatory symptom associated with SARS-CoV-19 infection in the patient.

The nicotinic receptor antagonist may be mecamylamine or an isomer of mecamylamine and the PPAR-γ agonist may be pioglitazone. Both the nicotinic receptor antagonist and the PPAR-γ agonist may be administered to the patient at a dose of about 2 mg/kg each.

In another embodiment, a method of decreasing severe acute respiratory syndrome coronavirus 2 (SARS CoV-2) infection in a patient in need thereof comprising: administering to the patient in need thereof a therapeutically effective amount of a composition comprising a nicotinic receptor antagonist wherein the nicotinic receptor antagonist is mecamylamine or an isomer thereof; a peroxisome proliferator activated receptor gamma (PPAR-γ) agonist wherein the PPAR-γ agonist is pioglitazone; and a pharmaceutically acceptable carrier. The nicotinic receptor antagonist, mecamylamine or mecamylamine isomer, and the PPAR-γ agonist, pioglitazone, act synergistically to reduce SARS-CoV-2 replication in virus-infected cells of the patient and also act synergistically to decrease inflammatory cytokine expression in the patient. The inflammatory cytokines may be selected from the group consisting of IL-6, IL-1β, TNFα, and combinations thereof.

The nicotinic receptor antagonist may be mecamylamine or an isomer of mecamylamine and the PPAR-γ agonist may be pioglitazone. Both the nicotinic receptor antagonist and the PPAR-γ agonist may be administered to the patient at a dose of about 2 mg/kg each.

In a further embodiment, a method of decreasing inflammatory cytokine expression in a patient infected with severe acute respiratory syndrome coronavirus 2 (SARS-CoV-2) comprising: administering to the patient in need thereof a therapeutically effective amount of a composition comprising a nicotinic receptor antagonist wherein the nicotinic receptor antagonist is mecamylamine or an isomer thereof; a peroxisome proliferator activated receptor gamma (PPAR-γ) agonist wherein the PPAR-γ agonist is pioglitazone; and a pharmaceutically acceptable carrier. The nicotinic receptor antagonist decreases inflammatory cytokine expression in the patient. The inflammatory cytokines may be selected from the group consisting of IL-6, IL-1β, TNFα, and combinations thereof. The nicotinic receptor antagonist, mecamylamine or mecamylamine isomer, and the PPAR-γ agonist, pioglitazone, act synergistically to decrease inflammatory cytokine expression in the patient.

The nicotinic receptor antagonist may be mecamylamine or an isomer of mecamylamine. Both the nicotinic receptor antagonist and the PPAR-γ agonist may be administered to the patient at a dose of about 2 mg/kg each.

BRIEF DESCRIPTION OF THE DRAWINGS

For a fuller understanding of the invention, reference should be made to the following detailed description, taken in connection with the accompanying drawings, in which:

FIG. 9 is a table depicting the calculation of the combination index for the in vivo mouse data of FIG. 8. The combination index, also known as CDI (coefficient of drug interaction) is calculated as follows: CDI=AB/(A×B). AB is the ratio of the 2-drug combination group to the control group. A or B is the ratio of the single drug group to the control group. CDI<1 indicates synergism, CDI=1 indicates additivity, and CDI>1 indicates antagonism.

DETAILED DESCRIPTION OF THE PREFERRED EMBODIMENT

Figure 1:
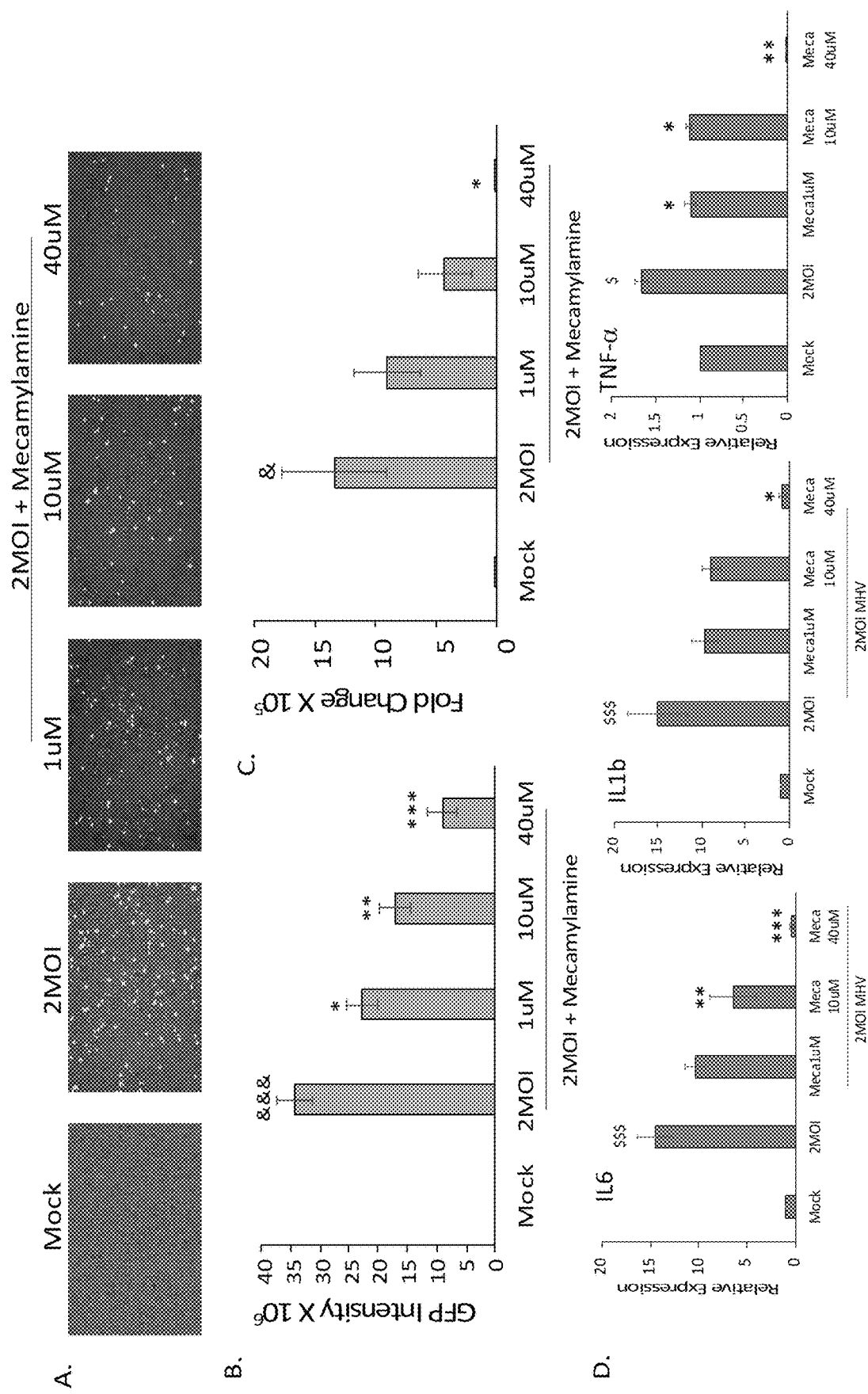
FIG. 1A-D are a series of images depicting treatment with mecamylamine reduces the MHV4 infection at 2 MOI in IMG cells after 48 hours using different doses (5, 10, 20, and 40 μM) of mecamylamine. A) photomicrographs showing GFP expression; B) histograms showing the percentage of GFP expressing cells; C) histograms showing the fold change in N gene expression; and D) histograms showing the fold change in inflammatory cytokine gene expression.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

As used herein, the singular forms "a," "an" and "the" include plural referents unless the context clearly dictates otherwise.

As used in this specification and the appended claims, the term "or" is generally employed in its sense including "and/or" unless the context clearly dictates otherwise.

All numerical designations, such as pH, temperature, time, concentration, and molecular weight, including ranges, are approximations which are varied up or down by increments of 1.0, 0.1, 0.01 or 0.001 as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, "about" means approximately or nearly and in the context of a numerical value or range set forth means±15% of the numerical.

As used herein "patient" is used to describe an animal, preferably a human, to whom treatment is administered, including prophylactic treatment with the compositions of the present invention. "Patient" and "subject" are used interchangeably herein.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

"Administering" or "administration" as used herein refers to the process by which the compositions of the present invention are delivered to the patient. The compositions may be administered in various ways, including but not limited to, orally, nasally, and parenterally.

A "therapeutically effective amount" as used herein is defined as concentrations or amounts of components which are sufficient to effect beneficial or desired clinical results, including, but not limited to, any one or more of treating symptoms of COVID-19 infection and preventing COVID-19 infection. Compositions of the present invention can be used to effect a favorable change in the condition whether that change is an improvement, such as stopping, reversing, or reducing COVID-19 infection, or a complete elimination of symptoms due to COVID-19 infection. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of the animal and the route of administration. In some embodiments, the effective amount may range from about 0.001 mg/kg to about 5 mg/kg of mecamylamine (or mecamylamine isomer) and/or pioglitazone per day, including all amounts in between. In some embodiments, the amount of mecamylamine (or mecamylamine isomer) and/or pioglitazone per day is about 2 mg/kg. The dose may be adjusted according to response.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used against viruses such as COVID-19. Additionally, compounds used in the present invention may be administered in combination with or concurrently with other therapeutics for COVID-19 or other respiratory viruses. A composition comprised of a therapeutically effective amount of both mecamylamine (or mecamylamine isomer) and pioglitazone was found to synergistically reduce SARS CoV-2 expression.

"Prevention" or "preventing" as used herein refers to any of: halting the effects of COVID-19 infection, reducing the effects of COVID-19 infection, reducing the incidence of COVID-19 infection, reducing the development of COVID-19 infection, delaying the onset of symptoms of COVID-19 infection, increasing the time to onset of symptoms of COVID-19 infection, and reducing the risk of development of COVID-19 infection.

"Treatment" or "treating" as used herein refers to any of the alleviation, amelioration, elimination and/or stabilization of a symptom, as well as delay in progression of a symptom of a particular disorder. For example, "treatment" of COVID-19 infection may include any one or more of the following: amelioration and/or elimination of one or more symptoms associated with COVID-19 infection, reduction of one or more symptoms of COVID-19 infection, stabilization of symptoms of COVID-19 infection, and delay in progression of one or more symptoms of COVID-19 infection. Treatment may include reduction of viral replication in cells and/or reducing inflammation associated with COVID-19 infection as shown through reduction in inflammatory cytokine expression.

"Infection" as used herein refers to the invasion of one or more microorganisms such as bacteria, viruses, fungi, yeast, or parasites in the body of a patient in which they are not normally present. In certain embodiments, the infection is from a respiratory virus such as SARS-CoV-2.

"Nicotinic receptor antagonists" as used herein refer to compounds that bind to nicotinic cholinergic receptors to inhibit the action of acetylcholine at the receptors. The compounds block synaptic transmission at autonomic ganglia, the skeletal neuromuscular junction and at CNS nicotinic synapses. Examples of nicotinic receptor antagonists useful herein include, but are not limited to, mecamylamine, gallamine triethiodide, bupropion, varenicline, dextromethorphan, atracurium besylate, pentolinium, tubocurarine, pancuronium, pipecuronium, vecuronium, methadone, metocurine iodide, rocuronium, doxacurium, mivacurium, metocurine, procaine, amobarbital, pentobarbital, butabarbital, butalbital, talbutal, secobarbital, metharbital, thiopental, primidone, methylphenobarbital, phenobarbital, aprobarbital, butobarbital, heptabarbital, hexobarbital, barbital, levacetylmethadol, cisatracurium, gantacurium, hexamethonium, isoflurane, amantadine, fluoxetine, 18-methoxycoronaridine, β-dihydroerythroidine, methyllycaconitine, chlorisondamine, trimethaphan, normecamylamine, N-(1,2,2) trimethyl-1-bicyclo[2,2,1]-heptylbenzenamine, dimethylaminoisocamphane, exo-aminonorbornane, 2,2,6,6-tetramethylpiperdine, 2,2,6,6-tetramethyl-4-aminopiperdine, pempidine, erysodine, phenyltropane carboxylic acid methyl esters, arylpempidine analogues, ibogaine, as well as stereoisomers, analogs or combinations thereof.

"PPAR-γ agonist" as used herein refers to an agent which modulates peroxisome proliferator-activated receptors (PPARs), in particular to repress the inflammatory process. Examples of PPARs useful herein include, but are not limited to, thiazolidinedione drugs, such as pioglitazone, rosiglitazone, and troglitazone, as well as stereoisomers, analogs, or combinations thereof. In some embodiments, pioglitazone, has been found to be efficacious in treating and/or preventing SARS-CoV-2 infection.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, atranorin or other polyphenolic lichen acid isolate, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration nasally, orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch.

COVID-19 infection, caused by the SARS-CoV-2 virus, can cause varying neurological, cardiovascular, respiratory, and inflammatory symptoms in patients. Respiratory symptoms have been well documented and include shortness of breath, difficulty breathing, and cough. Serious lung damage can be caused by COVID-19 infection due to inflammation in the lungs caused by an overexuberant immune response termed the cytokine storm. In addition, inflammation can cause multisystem inflammatory syndrome (MIS) in both adults and children. MIS is a rare, but serious, condition caused by COVID-19 infection in which various body parts become inflamed, such as the heart, lungs, kidneys, brain, skin, eyes, or gastrointestinal organs.

Cardiovascular symptoms such as dizziness, persistent pain or pressure in the chest, tachycardia, and heart palpitations have been reported in COVID-19 patients. In some extreme cases, post-viral heart failure and viral myocarditis have also been reported. Further, hypertension is known to be a comorbidity for COVID-19 infection.

Many patients infected with COVID-19 report having neurological symptoms such as anosmia, ageusia, nausea, impaired consciousness (i.e. "brain fog"), confusion, fatigue, and headache. For some patients, such neurological symptoms may persist for weeks to months after the patient has cleared the virus from their system as discussed below.

In some patients, COVID-19 symptoms may last for weeks or months despite testing negative for the virus. Such patients are termed "long haulers" and have, in theory, recovered from the worst impacts of COVID-19 infection, however, they still exhibit symptoms. These long haul symptoms can include neurological symptoms, such as brain fog, anosmia, ageusia, insomnia, and headaches. Some long haulers experience symptoms such as debilitating fatigue, body aches, and joint pain. Respiratory symptoms such as coughing and shortness of breath may also be present as long haul symptoms. Cardiovascular symptoms such as persistent pain or pressure in the chest, tachycardia, dizziness, and heart palpitations have also been reported. (Rubin, R., As their numbers grow, COVID-19 "long haulers" stump experts, *JAMA,* 2020, 324(14):1381-1383).

While it is unknown why long haulers continue to experience symptoms while testing negative for the SARS-CoV-2 virus, alleviation of the symptoms should be considered with any treatment regime. One theory is that the body remains in a heightened immune state after infection, possibly due to small amounts of virus remaining in the body. Therapeutics that are capable of reducing inflammation and/or neurological, respiratory or cardiovascular symptoms are needed.

As noted previously, mecamylamine is known for its cardiovascular effects. Mecamylamine is a well-known nicotine receptor antagonist that was first used as an antihypertensive medication. The drug blocks sympathetic ganglia transmission which results in vasodilation, a decrease in blood pressure, and reduction in heart rate. (Taylor, P., In: The Pharmacological Basis of Therapeutics, Goodman, L S and Gilman, A. eds., McMillan Publishing Co., New York City, pp. 193-95, 1996; Shytle, R D et al., Mecamylamine (Inversine®): an old antihypertensive with new research directions, *Journal of Human Hypertension,* 2002, 16:453-457).

In addition to its cardiovascular effects, mecamylamine is also known to exert neurological effects. Mecamylamine has the ability to cross the blood brain barrier and selectively antagonize neuronal nicotinic acetylcholine receptors (nAchR) at much lower doses than the effective hypertensive dose. Decreased dosages allow for avoidance of side effects associated with the drug's inhibition of parasympathetic activity. (Young, J. M. et al., Mecamylamine: New therapeutic uses and toxicity/risk profile, *Clinical Therapeutics,* 2001, 23(4):532-565). Mecamylamine has been reported to block CNS actions of nicotine, alter cognitive functioning, alter electrical brain waves, and alter cortical blood flow. (Martin, B R et al., Biochemical Pharmacology, 1989, 38:3391-3397; Newhouse, P A et al., Neuropsychopharmacology, 1994, 10:93-107; Pickworth, W B et al., Pharmacology Biochemistry & Behavior, 1988, 30:149-153; Gitalman, D R et al., Neurobiology, 1992, 13:313-318).

The present disclosure provides compositions and methods of treatment and prevention of COVID-19. The inventors submit that nicotinic receptor antagonists, particularly mecamylamine or isomers thereof, can be used in the treatment and/or prevention of COVID-19 infection by blocking these nAChR receptors thus preventing binding of the virus. The binding of the nicotinic receptor antagonist aids in the CNS response to COVID-19 symptoms such as headache, vomiting, anosmia, ageusia, brain fog, and nausea in both acute and long haul COVID-19 patients. Given that mecamylamine is well-known for its cardiovascular effects, administration of a therapeutically effective amount of mecamylamine, or an isomer thereof, can also alleviate cardiovascular symptoms such as tachycardia, palpitations, and chest pain in both acute and long haul patients. Administering lower doses of mecamylamine can avoid undesirable side effects while still being effective for treatment and/or prevention of the viral infection. Further, either a racemic mixture or either stereoisomer may be administered.

As noted previously, inflammation plays a significant role in symptoms experienced by both acute and long haul COVID-19 patients. COVID-19 infection can lead to uncontrolled inflammation, which in turn leads to a cytokine storm, i.e. an exaggerated release of cytokines in response to infection that is due to unregulated release of pro-inflammatory cytokines such as IL-6, IL-1β, and TNFα, among others.

Pioglitazone was previously found to inhibit secretion of pro-inflammatory cytokines and increase secretion of anti-inflammatory cytokines. (Qiu D, Li X N. Pioglitazone inhibits the secretion of proinflammatory cytokines and chemokines in astrocytes stimulated with lipopolysaccharide. Int J Clin Pharmacol Ther 2015 September; 53(9):746-52). Specifically, pioglitazone was found to significantly reduce IL-6 and TNFα mRNA expression to attenuate lung injury. (Kutsukake M, Matsutani T, Tamura K, et al. Pioglitazone attenuates lung injury by modulating adipose inflammation. J Surg Res. 2014; 189(2):295-303).

Administration of a therapeutically effective amount of pioglitazone can decrease inflammation by reducing the cytokine storm. As noted previously, pioglitazone acts to inhibit secretion of proinflammatory cytokines while promoting secretion of anti-inflammatory cytokines. This decrease in proinflammatory cytokines and promotion of anti-inflammatory cytokines aids in an anti-inflammatory response that can resolve inflammatory symptoms associated with COVID-19 infection in the respiratory system, as well as symptoms of other body systems, such as joint pain, body aches, and fatigue.

Surprisingly, the inventors found that a combination of an anti-inflammatory agent, such as the PPAR-γ agonist pioglitazone, with a nicotinic receptor antagonist, particularly mecamylamine or isomers thereof, was able to synergistically reduce viral replication of MHV4 in a murine model. Translating this to humans, this combination also suggests a similar synergistic effect on SARS-CoV-2 in humans. Such combination treatment is advantageous in that the therapeutic agents act together to reduce multiple neurological, cardiovascular and inflammatory symptoms caused by COVID-19 infection in both acute and long haul patients. Such symptoms include, but are not limited to, neurological symptoms such as headache, vomiting, anosmia, ageusia, brain fog, and nausea; cardiovascular symptoms such as heart palpitations, tachycardia, chest pain or pressure, hypertension, and dizziness; respiratory symptoms associated with lung inflammation such as shortness of breath and difficulty breathing; multisystem inflammatory syndrome (MIS); joint pain; body aches; and fatigue.

The following non-limiting examples illustrate exemplary systems and components thereof in accordance with various embodiments of the disclosure. The examples are merely illustrative and are not intended to limit the disclosure in any way.

Example 1—Treatment with Mecamylamine Decreases Viral Replication and Cytokine Expression The inventors treated mouse hepatitis virus strain 4 (MHV4) infected IMG cells with varying doses of mecamylamine to determine if the drug was efficacious in decreasing viral replication and cytokine expression associated with viral infection.

MHV is an excellent model for studying the pathogenesis, including tropism and virulence, as well as immune response to coronaviruses and was previously used as a model for SARS-CoV. There are several MHV strains which may be respiratory (polytropic) or enterotropic. MHV4 is a murine coronavirus having a spike protein and shares a common genus and similarities with SARS-CoV-2. MHV4 is a respiratory strain that initially replicates in the nasal respiratory and olfactory epithelium, with subsequent viremia and dissemination to the lungs as well as other organs. (Körner, R. W. et al., Of mice and men: the coronavirus MHV and mouse models as a translational approach to understand SARS-CoV-2, *Viruses,* Aug. 12, 2020, 12, 880).

While there are differences between the viruses that need to be addressed when studying murine models, use of MHV4 is an accepted model that can be translated to SARS-CoV-2 in humans. (Korner, R. W. et al., Of mice and men: the coronavirus MHV and mouse models as a translational approach to understand SARS-CoV-2, *Viruses,* Aug. 12, 2020, 12, 880).

Methods 200,000 IMG cells were plated per well in a 6 well plate. Cells were infected with 2

MOI live or UV inactivated MHV4 virus with low serum medium. After 4 h of infection cells were treated with 1, 10 or 40 µM mecamylamine for 48 hours. Images of GFP expression were taken using Keyence fluorescence microscope and quantitated using Image J software. Cells were lysed with Trizol reagent and total RNA was extracted from the lysates. cDNA were synthesized for downstream gene expression studies using appropriate primers. Statistical significance was calculated by one way ANOVA using Graph Pad Prism software.

Results

Following infection, the infected IMG cells expressed GFP whereas the mock infected cells did not show any GFP fluorescence. GFP expression was significantly reduced by mecamylamine showing a dose-dependent decrease of GFP expressing cells (FIGS. 1A and B) and dose-dependent decrease of MHV-4 N-gene expression (FIG. 1C). Also, qPCR analysis of cytokine gene expression showed dose-dependent decrease in cytokine gene transcription (FIG. 1D). Together the results indicate that mecamylamine is capable of decreasing SARS CoV-2 infection at relatively high doses.

Example 2—Docking Studies for Mecamylamine and Pioglitazone

Figure 2:
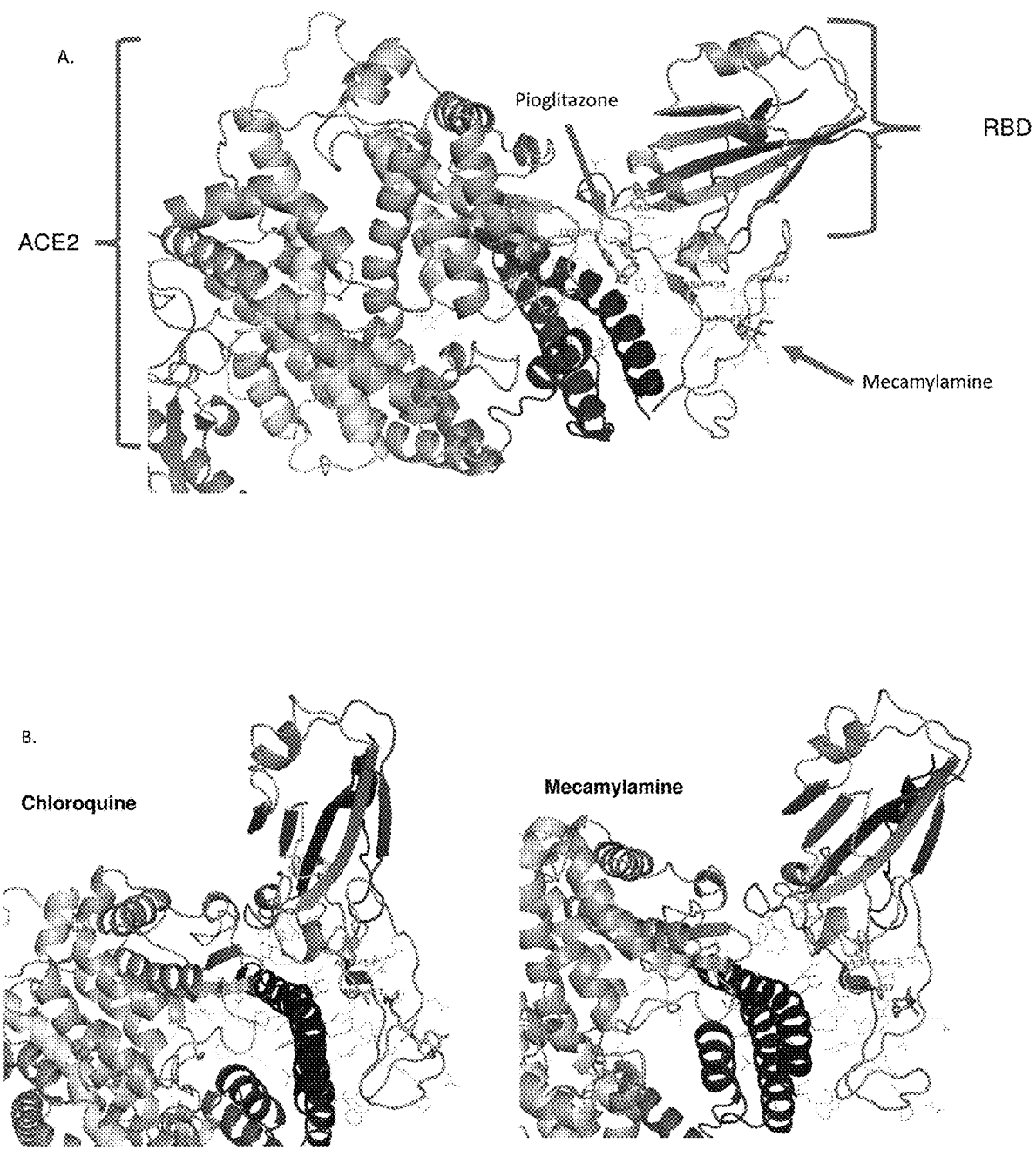
FIG. 2A-B are a series of images depicting molecular modeling of mecamylamine and SARS-CoV-2 spike protein interaction. A) spatial positions of mecamylamine and pioglitazone of their docking with SARS-CoV-2 spike protein; B) spatial positions of mecamylamine vs chloroquine docking with SARS-CoV-2 spike protein.
FIG. 2C is a table of binding scores and involved residues for mecamylamine and pioglitazone for their docking with SARS-CoV-2 spike protein.

The inventors conducted docking studies of chitosan (trimer) with the spike protein (6VYB) and spike protein bound to angiotensin-converting enzyme 2 (ACE2) (6LZG) using Molecular Operating Environment (MOE), a high throughput computational system by the chemical computing group which provides robust docking results. The docking studies were confined to the receptor binding domain (RBD) and exterior subdomains to make the analysis as homologous as possible, in an effort to increase the robustness of the results. Both pioglitazone, the FDA-approved antidiabetic drug as an anti-inflammatory candidate, and mecamylamine, as the anti-viral and antidepressant drug, were docked. Over 30 docking configurations were analyzed and the best poses taken from the data set are shown in FIG. 2.

The results show that pioglitazone and mecamylamine have clear distinctions of where they interact based on the spatial positions. These distinctions indicate a mecamylamine and pioglitazone combination treatment could prove effective in inhibiting SARS-COV2. Mecamylamine appears to target a similar site as chloroquine which was an early proposed inhibitor based on literature and reports. Pioglitazone has strong adherence to major interacting residues of SARS-COV2.

Example 3—Mecamylamine (Mec) and/or Pioglitazone (PG) Treatment Decreases MHV Replication on MHV4 Infected IMG Cells The inventors treated mouse hepatitis virus strain 4 (MHV4) infected IMG cells with varying doses of mecamylamine, 5 µM pioglitazone, or a combination of the two drugs to determine if the drugs were efficacious in decreasing viral replication.

Methods 200,000 IMG cells were plated per well in a 6 well plate. Cells were infected with 1MOI live or UV inactivated MHV4 virus with low serum medium. After 4 h of infection cells were treated with 5 µM pioglitazone (PG) or 1, 2.5 or 5 µM mecamylamine or a combination of PG (5 µM) and 1, 2.5 or 5 µM mecamylamine for 48 hours. Images of GFP expression were taken using Keyence fluorescence microscope and quantitated using Image J software. Cells were lysed with Trizol reagent and total RNA was extracted from the lysates. cDNA were synthesized for downstream gene expression studies using appropriate primers. Statistical significance was calculated by one way ANOVA using Graph Pad Prism software.

Results

Figure 3:
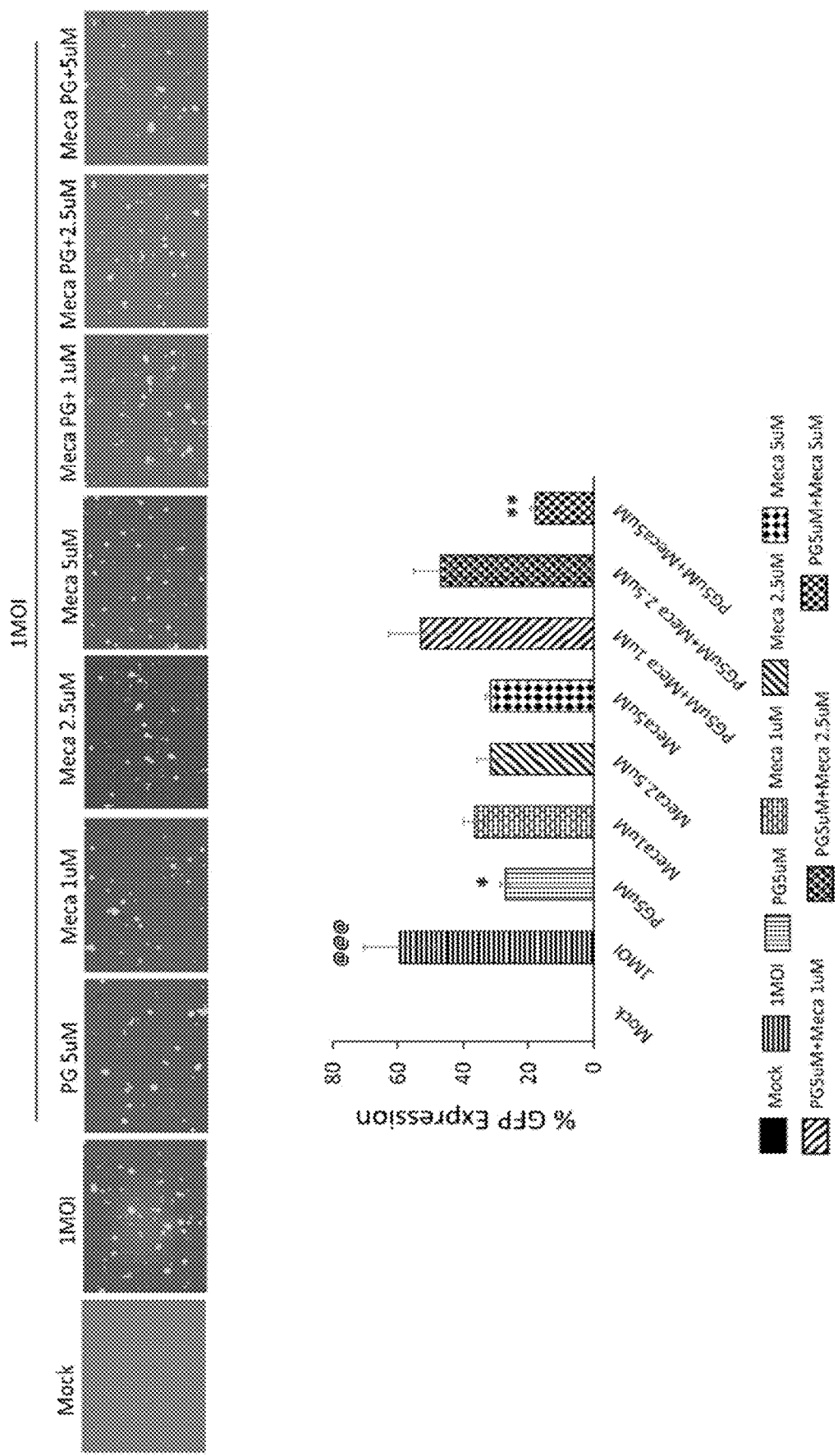
FIG. 3 is a series of images depicting Mecamylamine and Pioglitazone (PG) combination treatment reduces the MHV4 infection in IMG cells after 48 hours. Upper panel, photomicrographs showing GFP expression, Lower panel, histograms showing the percentage of GFP expressing cells. @@@$p<0.001$ vs mock, *$p<0.05$ vs 1MOI, **$p<0.01$ vs 1 MOI, magnification 200×.

Following infection, the infected IMG cells expressed GFP whereas the mock infected cells did not show any GFP fluorescence. GFP expression was significantly reduced by PG treatment as well as by PG and Mecamylamine 5 µM combination treatment (FIG. 3).

The gene expression analysis shows an increase in MHV nucleoprotein expression following infection with live viruses. MHVN expression was significantly reduced in single and combination treated groups except the PG+Mec 1 µM group, indicating efficacy of the treatments. In addition, PG+Mec 5 µM treatment significantly reduced MHVN expression as compared to PG+Mec 1 µM treatment (FIG. 3).

Example 4—Mecamylamine (Mec) and/or Pioglitazone (PG) Treatment Decreases Cytokine Expression on MHV4 Infected IMG Cells To investigate the effect of the treatments on inflammatory cytokine expression by IMG cells in vitro, gene expression of IL1β, IL6 and TNFα was studied.

Methods 200,000 IMG cells were plated per well in a 6 well plate. Cells were infected with 1MOI live or UV inactivated MHV4 virus with low serum medium. After 4 h of infection cells were treated with 5 µM pioglitazone (PG) or 1, 2.5 or 5 µM mecamylamine or a combination of PG (5 µM) and 1, 2.5 or 5 µM mecamylamine for 48 hours. Images of GFP expression were taken using Keyence fluorescence microscope and quantitated using Image J software. Cells were lysed with Trizol reagent and total RNA was extracted from the lysates. cDNA were synthesized for downstream gene expression studies using appropriate primers. Statistical significance was calculated by one way ANOVA using Graph Pad Prism software.

Results

Figure 4:
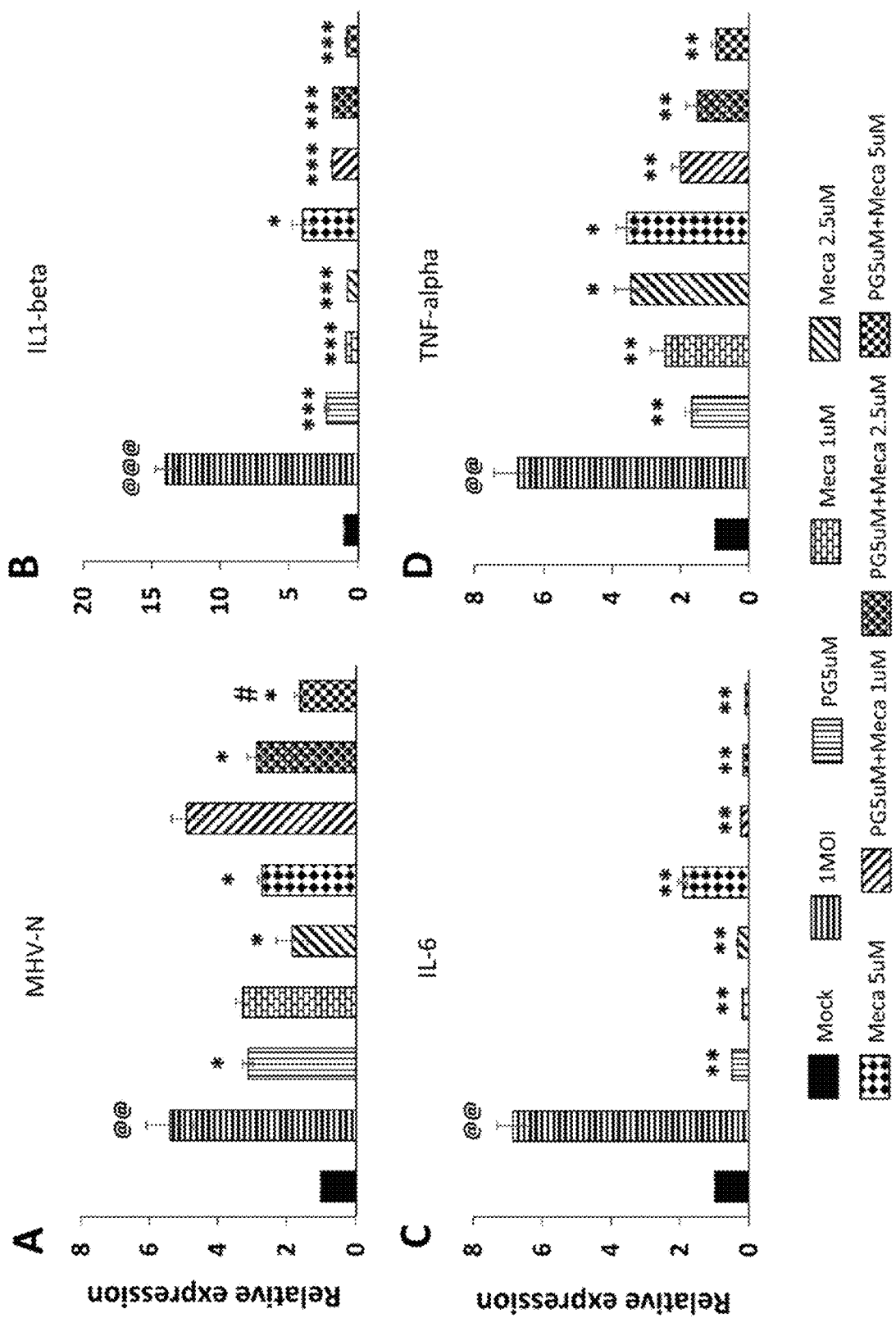
FIG. 4A-D are a series of graphs depicting PG-Mecamylamine treatment reduces the MHV4 infection and inflammatory cytokine release in IMG cells after 48 hours. Gene expression analysis showing the changes in relative expression in different treatment groups. A) MHV-N; B) IL1-β; C) IL-6; and D) TNF-α. @@$p<0.001$ vs mock, @@@, $p<0.001$ vs mock, *$p<0.05$ vs 1MOI, $p<0.01$ vs 1 MOI, *$p<0.001$ vs 1MOI, #$p<0.05$ vs PG+Meca 1 μM.

As shown in FIG. 4, all of the cytokine gene expressions were significantly reduced as compared with the untreated infected group. These results indicate that both drugs at all concentrations studied, as well as the combination of drugs, were able to decrease cytokine expression of MHV4, and translationally, SARS-CoV-2. This reduction in cytokine expression indicates the given treatments ability as therapeutics for SARS-CoV-19 infection in humans.

Example 5—Mecamylamine (Mec) and/or PG Treatment Decreases SARS-COV-2 Replication on Virus Infected Calu-3 Cells The inventors next tested the effects of mecamylamine and/or pioglitazone on SARS-CoV-2 infection of Calu cells in vitro.

Methods

Calu3 cells were infected with 0.1 MOI SARS CoV2 and treated with Pioglitazone (PG, 20 µM) and/or Mecamylamine (Mec, 5 µM) or Mecamylamine isomer (Mec iso, 5 µM) for 48 hrs. Post 48 hrs the infection the cells were collected in Trizol and RNA was extracted for PCR analysis.

Results

Figure 5:
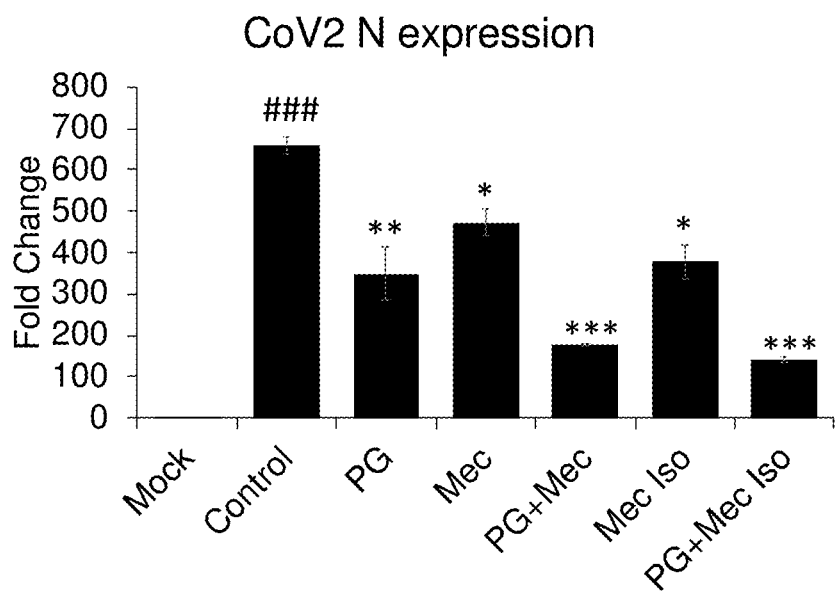
FIG. 5 is a graph depicting PG-Mecamylamine treatment reduces the SARS-CoV-2 replication. Calu3 cells were infected with 0.1 MOI SARS CoV2 and treated with Pioglitazone (PG, 20 μM) and/or Mecamylamine (Mec, 5 μM) or Mecamylamine isomer (Mec iso, 5 μM) for 48 hrs. Post 48 hrs the infection the cells were collected in Trizol and RNA was extracted for PCR analysis. The histogram presents the fold change of SARS CoV2 N protein expression., n=3, Data expressed as mean±SEM, Mock-UV inactivated, $^{\#}$ compared to Mock, * compared to control, *$p<0.05$, $p<0.005$, $^{\#\#\#,*}p<0.0005$.

The results showed that combination of PG and Mec or Mec isomer synergistically decreases the SARS CoV2 infection in Calu3 cells. The analysis of fold change of SARS CoV2 N protein expression showed that combination therapy synergistically decreases viral replication as compared to treatment with a single agent (FIG. 5).

Figure 6:
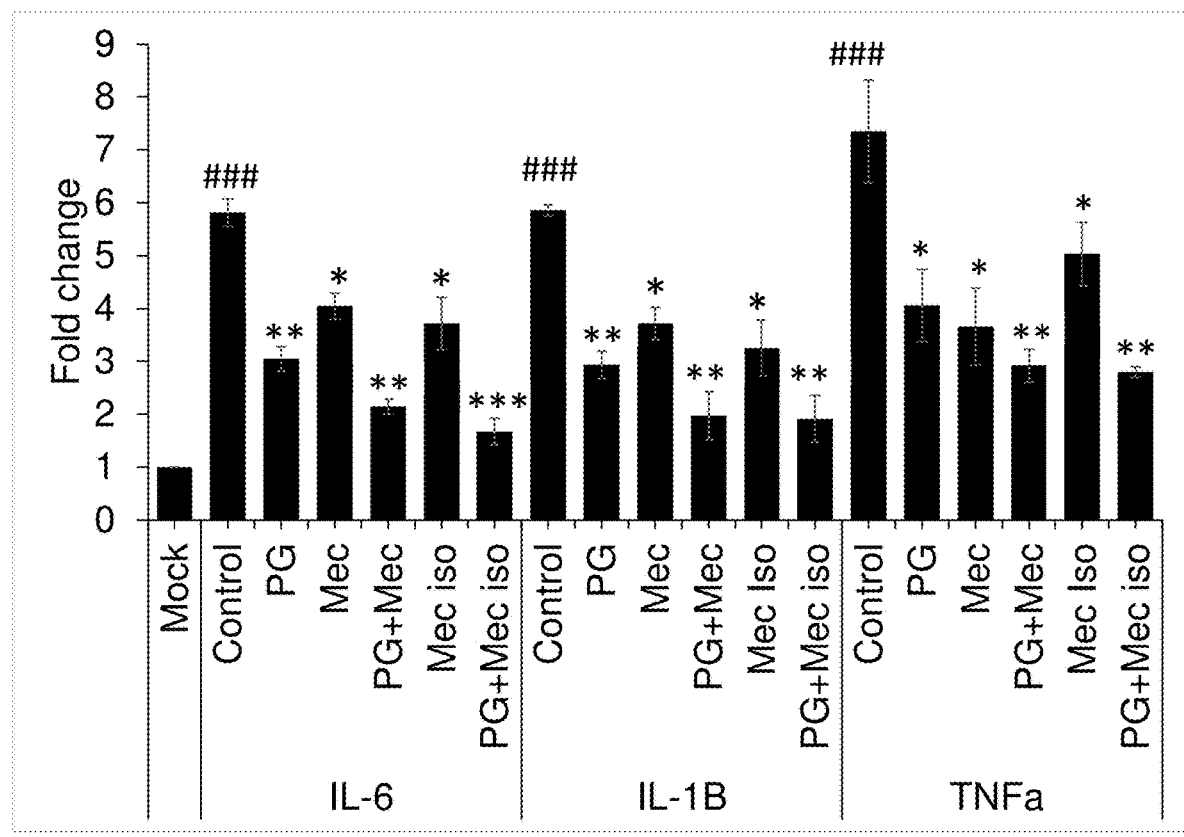
FIG. 6 is a graph depicting Mecamylamine and Pioglitazone combination treatment reduces the SARS-CoV-2 infection induced cytokine storm. The mRNA expression level of pro-inflammatory genes was assessed by qPCR, from RNA samples isolated from Calu 3 cells infected with SARS CoV2. Cells were collected 48 hrs of post infection with CoV2 virus (0.1 MOI) (Control-only infection) and treatment with Pioglitazone (PG, 20 μM) and/or Mecamylamine (Mec, 5 μM) or Mecamylamine isomer (Mec iso, 5 μM) for 48 hrs, n=3, Data expressed as mean±SEM, #Compared to blank (Mock), * Compared to control $^{\#,*}p<0.05$, $^{\#\#,}p<0.005$, $^{\#\#\#,*}p<0.0005$.

Example 6—Mecamylamine (Mec) and/or Pioglitazone (PG) Treatment Decreases SARS-COV-2 Infection Induced Cytokine Gene Expression on Virus Infected Calu-3 Cells The inventors tested administration of Mecamylamine and/or PG on SARS-CoV-2 infection of Calu cells in vitro to determine effects of the drug(s) on cytokine expression.
Methods
Calu3 cells were infected with 0.1 MOI SARS CoV2 and treated with Pioglitazone (PG, 20 µM) and/or Mecamylamine (Mec, 5 µM) or Mecamylamine isomer (Mec iso, 5 µM) for 48 hrs. Post 48 hrs the infection the cells were collected in Trizol and RNA was extracted for PCR analysis.
Results
The results show that mecamylamine, mecamylamine isomer and pioglitazone each separately exert a significant decrease on inflammatory cytokines IL-6, IL-1β, and TNFα. However, the combination therapy exhibited a synergistic decrease in inflammatory cytokines such as IL-1β, IL-6 and TNFα as compared to treatment with a single agent (FIG. 6).

Figure 7:
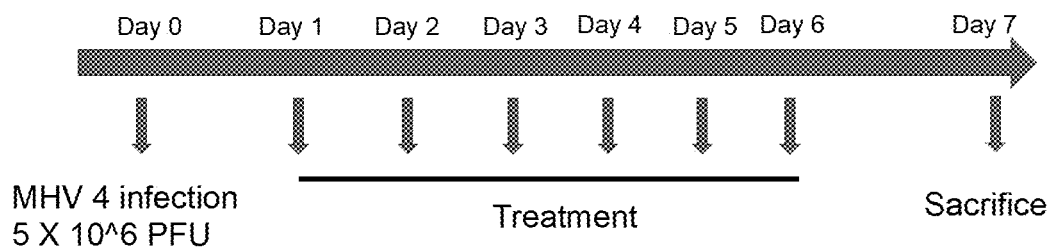
FIG. 7 is an image depicting the experimental design of an in vivo study in mouse coronavirus infection model.
Figure 8:
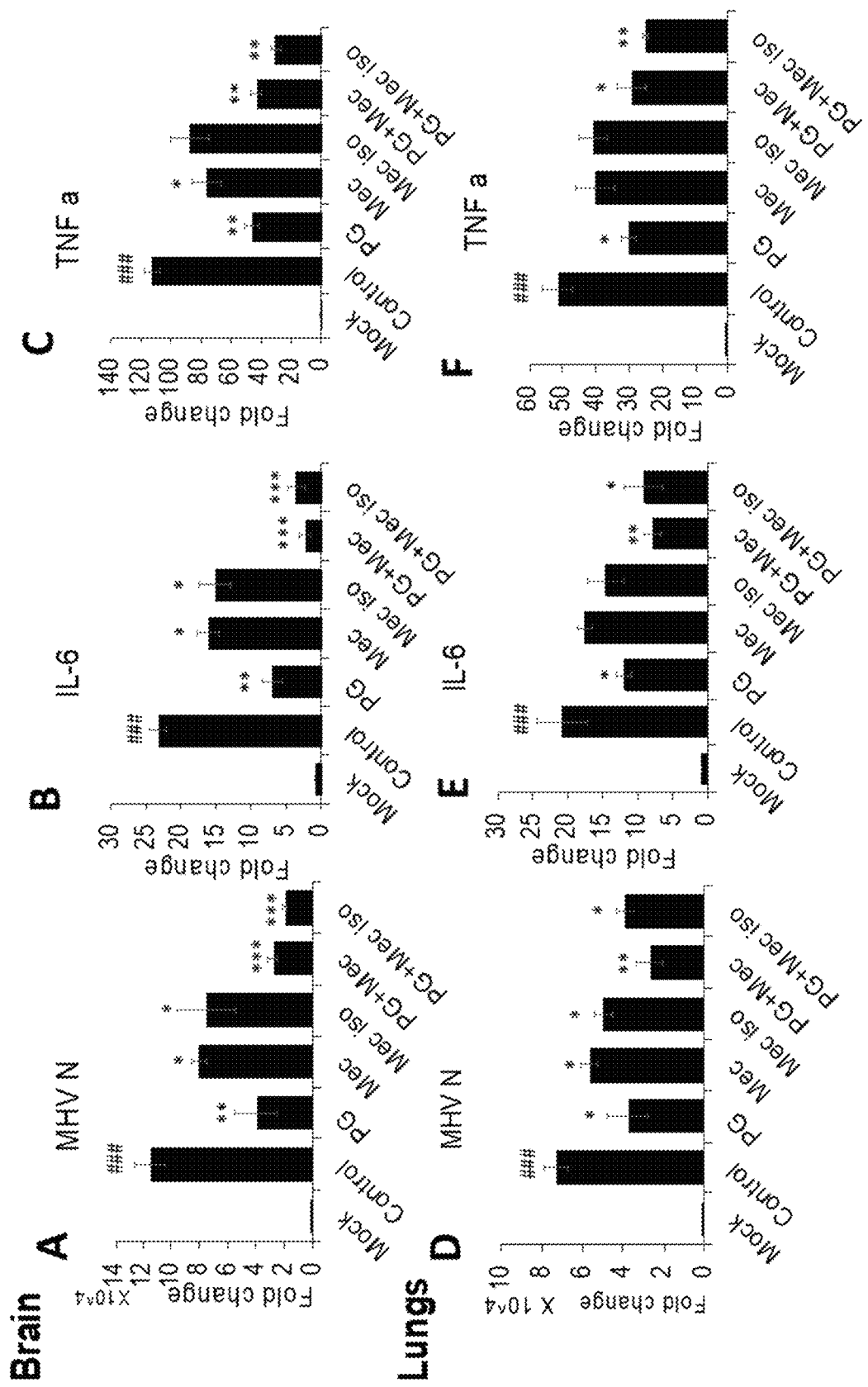
FIG. 8A-F are a series of images depicting histograms of mRNA expression level of MHV N protein and pro inflammatory genes (IL-6 and TNFα) assessed by qPCR, from RNA samples isolated from lung and brain samples from MHV4 infected C57bl/6 mice. A) MHV N protein in brain; B) IL-6 in brain; C) TNFα in brain; D) MHV N protein in lungs; E) IL-6 in brain; and F) TNFα in lungs. Mice were infected with 5×10$^6$ PFU and treated for 6 days post infection with (PG) pioglitazone (2 mg/kg) and/or (Mec) mecamylamine (2 mg/kg)/(Mec iso) mecamylamine isomer (2 mg/kg). At 7 days post infection the animals were sacrificed, and samples were collected, Mock-UV inactivated virus, n=3 Data expressed as mean±SEM, * Compared to Mock, $^{\#}$ Compared to Mock *$p<0.05$, $p<0.005$, $^{\#\#\#,*}p<0.0005$.

Example 7—Mecamylamine (Mec) and/or Pioglitazone (PG) Treatment Decreases MHV Infection in Virus Infected Mice To investigate whether Mecamylamine and/or PG treatment decreases MHV infection induced viral replication, the inventors examined the effect of these drugs alone or in combination on the viral infection in mice.
Methods
The protocol is schematically described in FIG. 7. Briefly, mice were intranasally inoculated with 5 X 106 PFU of MHV 4 virus. They were treated thereafter once daily with a drug(s) comprising mecamylamine (2 mg/kg) or mecamylamine isomer (Mec Iso) (2 mg/kg) and/or PG (2 mg/kg) for a 5 day period. On day 7, mice were sacrificed and their lung mRNA isolated for qPCR analysis of MHV-4 N gene expression and expression of the inflammatory cytokine genes in brain and in lung tissues.
Results
The results show that the mecamylamine (or mecamylamine isomer) and pioglitazone combination treatment (2 mg/kg of each drug) showed a greater reduction in the expression of N gene and the inflammatory cytokines as compared to treatment with a single agent. (FIG. 8) These results indicate the combination treatment can synergistically decrease viral replication and cytokine storm in both the brain and lung.
FIG. 9 depicts a calculation of the combination index for the in vivo mouse data of FIG. 8. The combination index, also known as CDI (coefficient of drug interaction) is calculated as follows: CDI=AB/(A×B). AB is the ratio of the 2-drug combination group to the control group. A or B is the ratio of the single drug group to the control group. CDI<1 indicates synergism, CDI=1 indicates additivity, and CDI>1 indicates antagonism. As shown in the image, the combination of PG with Mec or Mec isomer exhibited a synergistic result. The synergism of these drug combinations in reducing SARS-CoV-2 infection suggests their applicability as an efficacious therapy against COVID-19.

Example 8—Treatment with Combination of Mecamylamine and Pioglitazone (Prophetic)

A 49 year old male patient presents with headache, vomiting, nausea, and loss of taste and smell. A diagnosis of COVID-19 is confirmed. The patient is administered a therapeutically effective amount of a composition comprising the combination of the nicotinic receptor antagonist mecamylamine and the drug pioglitazone for a time period sufficient to alleviate the symptoms. The patient is retested twice over a several week timespan and tests negative for the virus.

Example 9—Treatment with Combination of Mecamylamine Isomer and Pioglitazone (Prophetic)

A 35 year old female patient presents with headache, sore throat, coughing, and loss of taste and smell. A diagnosis of COVID-19 is confirmed. The patient is administered a therapeutically effective amount of a composition comprising the combination of mecamylamine isomer and pioglitazone for a time period sufficient to alleviate the symptoms. The patient is retested twice over a several week timespan and tests negative for the virus.

Example 10—Prophylactic Treatment with Combination of Mecamylamine and Pioglitazone (Prophetic)

A 40 year old female tests negative for COVID-19 and is administered a therapeutically effective amount of a composition comprising the combination of the nicotinic receptor antagonist mecamylamine and the drug pioglitazone as a preventative to infection by the virus. The female is exposed to COVID-19 through contact with multiple people infected with the virus. The female does not develop a COVID-19 infection as confirmed by testing.

Example 11—Prophylactic Treatment with Mecamylamine Isomer and Pioglitazone (Prophetic)

A 29 year old male presents with coughing, sore throat, and fever. A diagnosis of COVID-19 is confirmed and the patient is administered a therapeutically effective amount of a composition comprising mecamylamine for a time period sufficient to alleviate the symptoms. The patient is retested twice over a several week timespan and tests negative for the virus.

CONCLUSION

The inventors have discovered both the nicotinic receptor antagonist mecamylamine, and isomers thereof, as well as the PPAR-γ agonist pioglitazone are effective in reducing inflammatory cytokine expression as well as reducing viral replication of SARS-CoV-2 in virus-infected cells. However, the inventors unexpectedly found that the combination of mecamylamine (or isomers thereof) with pioglitazone had a synergistic effect on the reduction of both inflammatory cytokine expression as well as viral replication of SARS-CoV-2 in virus-infected cells. These results indicate a combination therapy of mecamylamine (or isomers thereof) with pioglitazone can be effective in treating SAR-CoV-2 infection in humans.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating severe acute respiratory syndrome coronavirus 2 (SARS-CoV-2) in a patient in need thereof comprising:
    administering to the patient in need thereof a therapeutically effective amount of a composition comprising
        a nicotinic receptor antagonist wherein the nicotinic receptor antagonist is mecamylamine or a stereoisomer thereof;
        a peroxisome proliferator activated receptor gamma (PPAR-γ) agonist wherein the PPAR-γ agonist is pioglitazone; and
        a pharmaceutically acceptable carrier;
    wherein the nicotinic receptor antagonist and the PPAR-γ agonist act synergistically to treat the SARS-CoV-2 in the patient by reducing cytokine storm caused by inflammatory cytokine overexpression.

2. The method of claim 1, wherein the nicotinic receptor antagonist is administered to the patient at a dose of about 2 mg/kg.

3. The method of claim 1, wherein the PPAR-γ agonist is administered to the patient at a dose of about 2 mg/kg.

4. The method of claim 1, wherein at least one neurological, cardiovascular, or inflammatory symptom of the SARS-CoV-2 infection is reduced by administration of the composition to the patient.

5. A method of decreasing severe acute respiratory syndrome coronavirus 2 (SARS CoV-2) infection in a patient in need thereof comprising:
    administering to the patient in need thereof a therapeutically effective amount of a composition comprising
        a nicotinic receptor antagonist wherein the nicotinic receptor antagonist is mecamylamine or a stereoisomer thereof;
        a peroxisome proliferator activated receptor gamma (PPAR-γ) agonist wherein the PPAR-γ agonist is pioglitazone; and
        a pharmaceutically acceptable carrier;
    wherein the nicotinic receptor antagonist and the PPAR-γ agonist act synergistically to reduce cytokine storm caused by inflammatory cytokine overexpression and SARS-CoV-2 replication in virus-infected cells of the patient.

6. The method of claim 5, wherein the nicotinic receptor antagonist is administered to the patient at a dose of about 2 mg/kg.

7. The method of claim 5, wherein the PPAR-γ agonist is administered to the patient at a dose of about 2 mg/kg.

8. The method of claim 5, wherein the inflammatory cytokines are selected from the group consisting of IL-6, IL-1β, TNFα, and combinations thereof.

9. A method of decreasing inflammatory cytokine expression in a patient infected with severe acute respiratory syndrome coronavirus 2 (SARS-CoV-2) comprising:
    administering to the patient in need thereof a therapeutically effective amount of a composition comprising
        a nicotinic receptor antagonist wherein the nicotinic receptor antagonist is mecamylamine or a stereoisomer thereof;
        a peroxisome proliferator activated receptor gamma (PPAR-γ) agonist wherein the PPAR-γ agonist is pioglitazone; and
        a pharmaceutically acceptable carrier;
    wherein the nicotinic receptor antagonist and the PPAR-γ agonist act synergistically to decrease the inflammatory cytokine expression in the patient.

10. The method of claim 9, wherein the PPAR-γ agonist is administered to the patient at a dose of about 2 mg/kg.

11. The method of claim 9, wherein the nicotinic receptor antagonist is administered to the patient at a dose of about 2 mg/kg.

12. The method of claim 9, wherein the inflammatory cytokines are selected from the group consisting of IL-6, IL-1β, TNFα, and combinations thereof.

* * * * *